United States Patent
Mays

(10) Patent No.: US 6,644,972 B1
(45) Date of Patent: *Nov. 11, 2003

(54) ENDODONTIC OBTURATOR WITH REMOVABLE CARRIER AND METHOD OF USE THEREOF

(76) Inventor: Ralph C. Mays, 5436 S. Mingo Rd., Tulsa, OK (US) 74146

(*) Notice: Subject to any disclaimer, the term of this patent is extended or adjusted under 35 U.S.C. 154(b) by 16 days.

This patent is subject to a terminal disclaimer.

(21) Appl. No.: 09/925,988

(22) Filed: Aug. 9, 2001

Related U.S. Application Data

(63) Continuation of application No. 09/481,611, filed on Jan. 12, 2000, now Pat. No. 6,312,261.

(51) Int. Cl.$^7$ ................................................ A61C 5/02
(52) U.S. Cl. ................................ 433/224; 433/81
(58) Field of Search ........................... 433/224, 32, 81, 433/164

(56) References Cited

U.S. PATENT DOCUMENTS

| | | | |
|---|---|---|---|
| 674,419 A | 5/1901 | Kinsman | 433/224 |
| 1,463,963 A | 8/1923 | Miller | 433/224 |
| 1,469,992 A | 10/1923 | Card | 433/81 |
| 1,969,808 A | 8/1934 | Lentulo | 433/164 |
| 3,318,000 A | 5/1967 | Paris | 433/224 |
| 3,534,476 A | 10/1970 | Winters | 433/224 |
| 3,813,779 A | 6/1974 | Tosti | 433/214 |
| 3,861,043 A | 1/1975 | Lieb et al. | 433/225 |
| 4,353,698 A | 10/1982 | McSpadden | 433/164 |
| 4,397,634 A | 8/1983 | Biggs | 433/225 |
| 4,457,710 A | 7/1984 | McSpadden | 433/81 |
| 4,480,996 A | 11/1984 | Crovatto | 433/164 |
| 4,525,147 A * | 6/1985 | Pitz et al. | 433/224 |
| 4,681,545 A * | 7/1987 | Lapcevic | 433/224 |
| 4,758,156 A | 7/1988 | Johnson | 433/81 |
| 4,971,556 A * | 11/1990 | Ritano | 433/102 |
| 5,051,093 A | 9/1991 | Fitzmorris | 433/244 |
| 5,302,129 A * | 4/1994 | Heath et al. | 433/224 |
| 5,350,298 A * | 9/1994 | Delaire | 433/81 |

FOREIGN PATENT DOCUMENTS

| | | |
|---|---|---|
| CA | 1220369 | 4/1987 |
| CH | 513640 | 11/1971 |
| DE | 126184 | 12/2001 |
| FR | 775073 | 12/1934 |
| FR | 2163953 | 7/1973 |

OTHER PUBLICATIONS

Jun. 1978– Journal of Endodontics vol. 4, No. 6.
*The Dental Cosmos*– New York Odontological Society vol. XXV, P. 185–195.
*Obturation of the Radicular Space* by Ingle and Taintor–Endodontics Third Edition, P. 271–272.
*A Newly Designed Root Canal Filling Material* by Negm, Grant et al.– British Dental Journal, Jan. 1, 1980.
*Filling Root Canals with Silver–Percha Cones: A Clinical Study* by Negm– Oral Surgery, Jan. 1983.

* cited by examiner

Primary Examiner—John J. Wilson
(74) Attorney, Agent, or Firm—Gable & Gotwals; Paul H. Johnson

(57) ABSTRACT

A method of filing an endodontically prepared root canal includes the steps of applying filler material to a distal portion of an elongated shaft formed of heat conducting material, inserting the proximal portion of the shaft having the filler material thereon into the root canal, heating the shaft to decrease the surface tension of the filler material and removing the shaft leaving the filler material in the root canal. An obturator system for practicing the method of filling an endodontically prepared root canal employs an elongated heat conductible shaft having proximal and distal portions with filler material on the distal portion, the distal portion of the shaft with the filler material thereon being insertable into a tooth root canal and a heat source serving to selectably heat the shaft allowing it to be removed while leaving the filler material in the root canal.

14 Claims, 5 Drawing Sheets

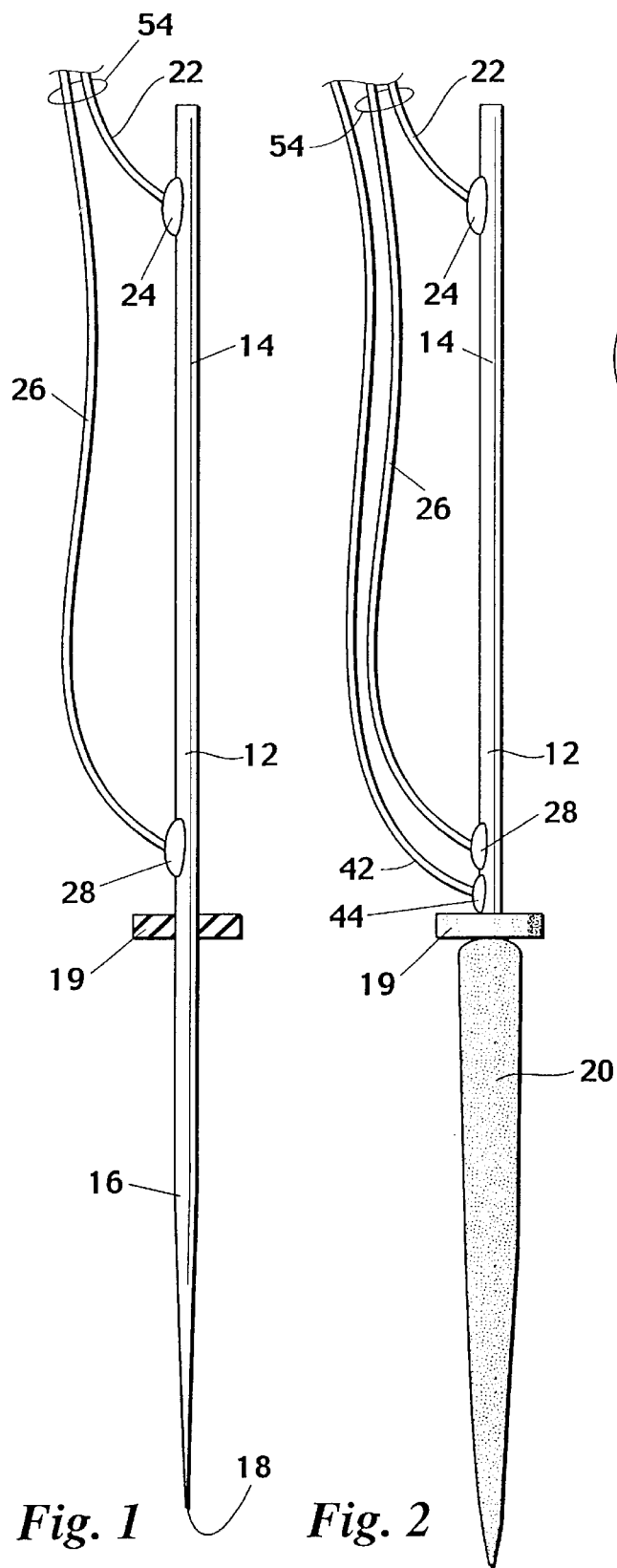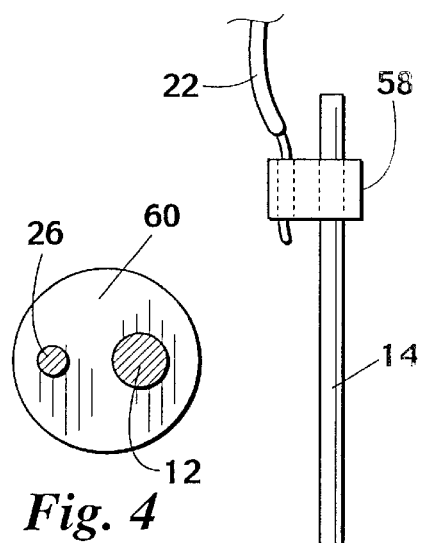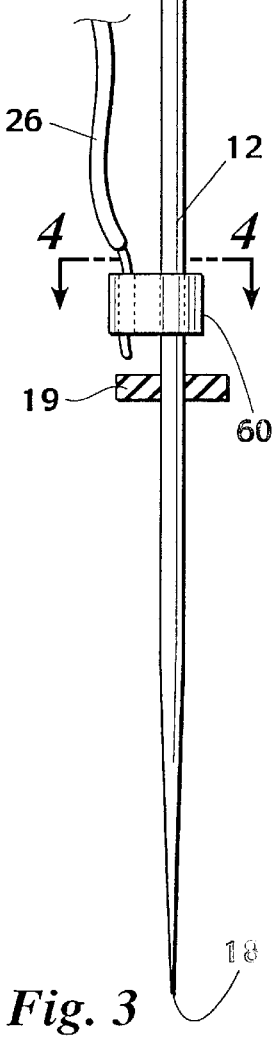

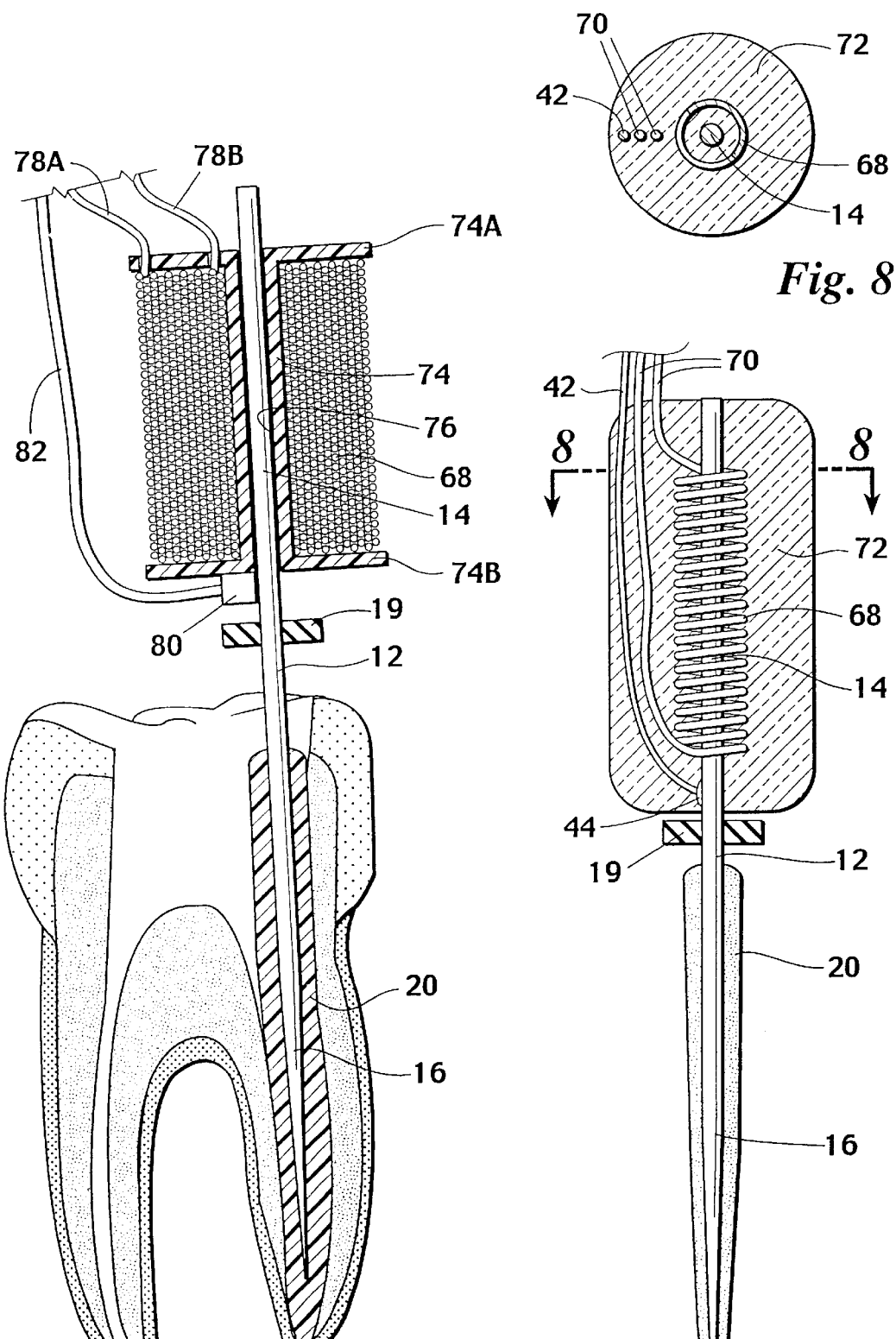

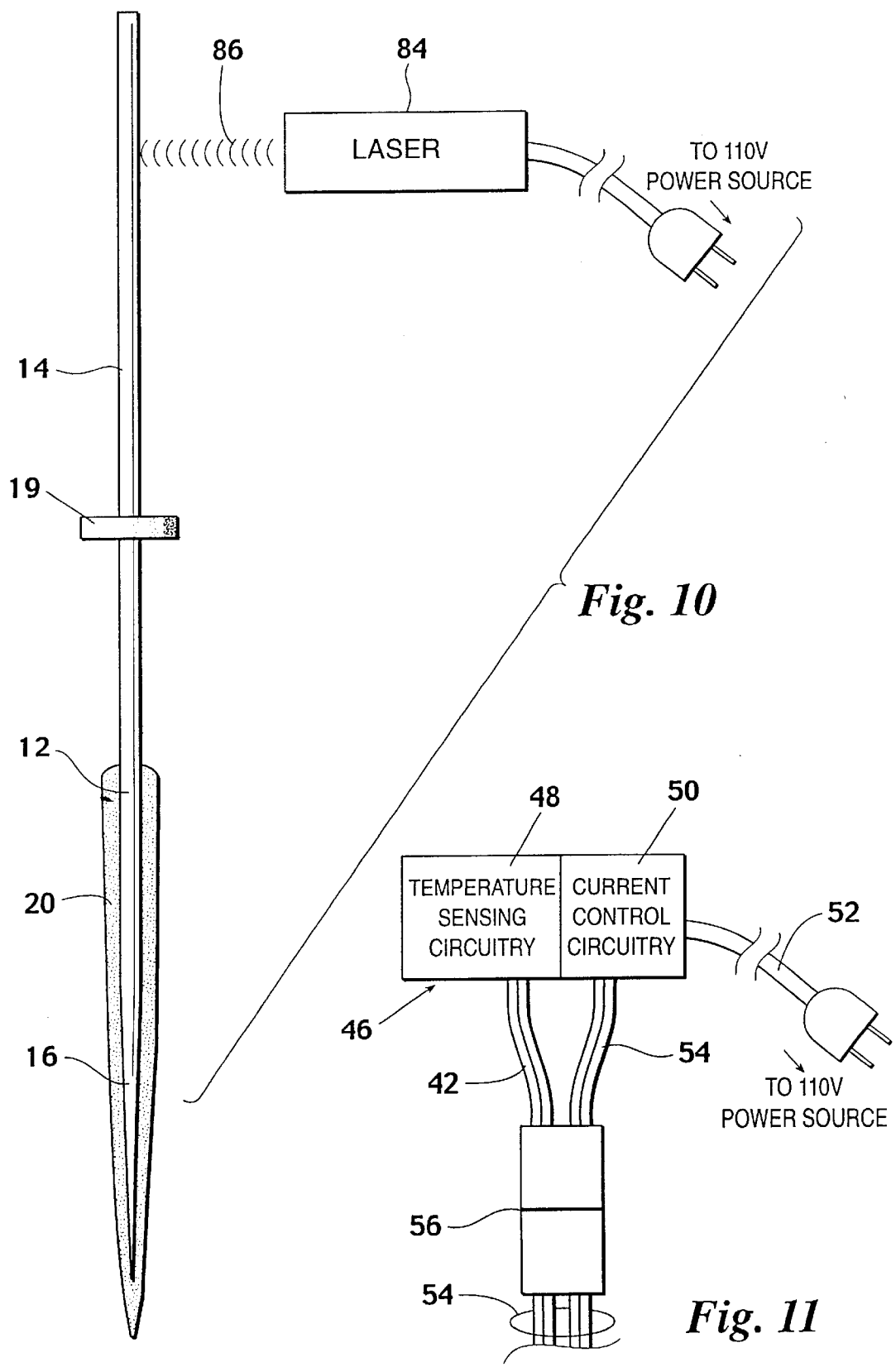

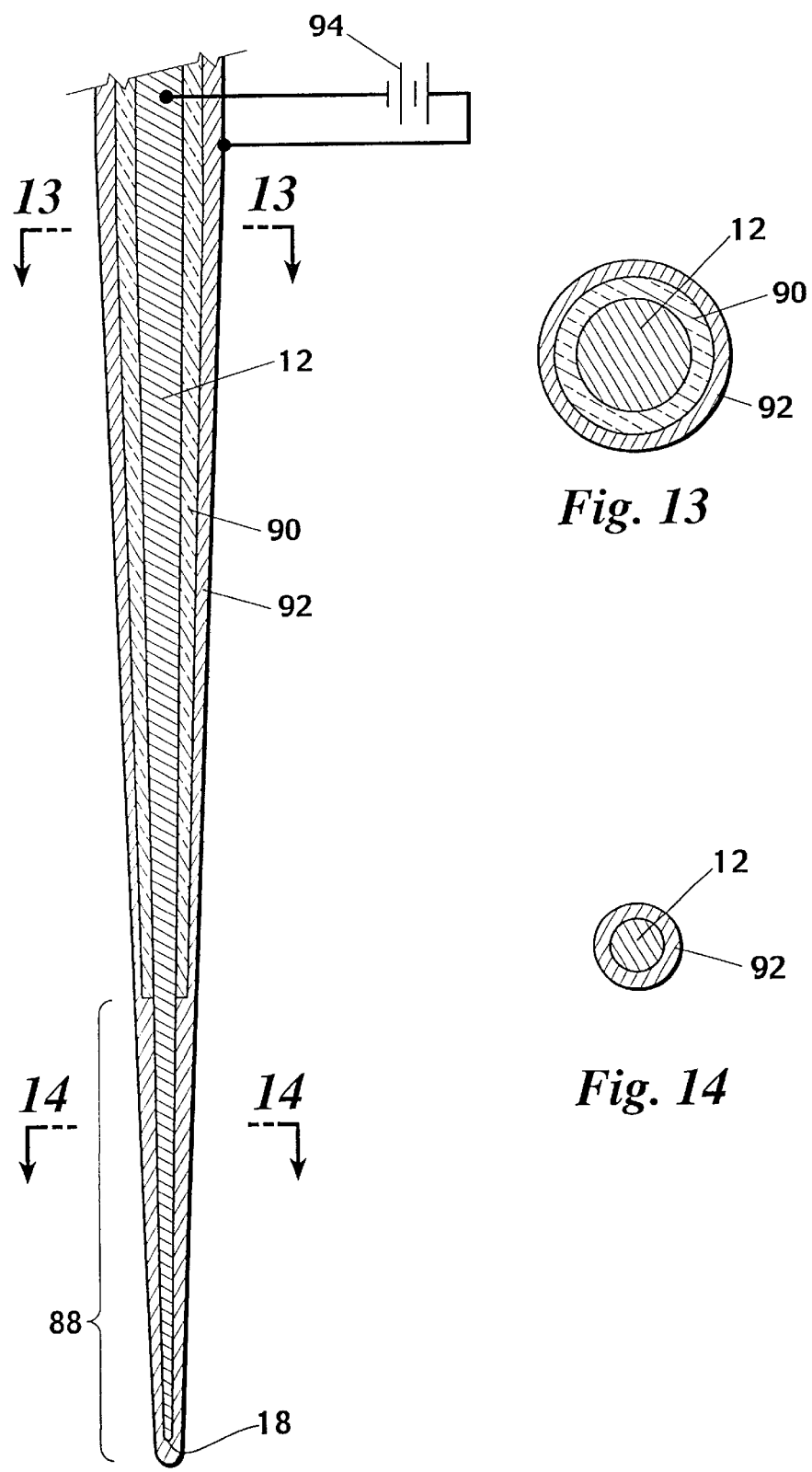

ENDODONTIC OBTURATOR WITH REMOVABLE CARRIER AND METHOD OF USE THEREOF

This application is a continuation of application Ser. No. 09/481,611, filed Jan. 12, 2000, now U.S. Pat. No. 6,312,261.

REFERENCE TO PENDING APPLICATIONS

This application is not related to any pending United States or international patent application.

REFERENCE TO MICROFICHE APPENDIX

This application is not referenced in any Microfiche Appendix.

BACKGROUND OF THE INVENTION

One of the greatest improvements made in dentistry in this century is the use of endodontics to save natural teeth that become abscessed. In the past, when the root canal of a tooth became abscessed, a fairly frequent occurrence, a dentist could relieve the intense pain produced by the abscessed tooth only by extracting the tooth. In the last couple of decades, procedures have been improved to the point that by the practice of endodontics, most abscessed teeth can now be saved.

Endodontics in general consists of treating an abscessed tooth to relieve the abscess by cleaning out the nerve and pulpal tissue in the tooth root canal so as to remove the material that is the source of infection and thereby remove the infection itself from within the tooth and from within the patient's system.

The typical procedure for treating an abscessed tooth in the modern dental practice is to drill a hole through the coronal area to access the upper end of the root canal. The dentist, or endodontic practitioner, then carefully removes the nerve and pulpal tissue from the root canal and shapes the root canal for receiving an inert filler material. Removal of pulpal material and shaping the root canal is accomplished by the use of dental files that are inserted through the opening in the coronal area and manipulated to scrape away and remove pulpal material and at the same time shape the canal to receive the filler material. After a canal has been cleared of pulpal material it must be filled with an inert material to prevent, or at least substantially reduce the possibility of fluids and material from the body entering into the root canal through the root apical area. The standard filler material that has been in use by dentists and endodontists for many years is gutta percha, a naturally occurring plastic-like material that has characteristics that particularly adapt it for use as a filler material although other types of filler materials have been and in the future undoubtedly will be developed.

Effectively filling a cleaned and prepared root canal is an essential step in a successful endodontic operation. Filler material can be injected directly into a root canal such as by means of a manually employed compacting instrument. Others have suggested the use of mechanical injection devices for injecting filler material directly into the root canal. One of the most successful ways of filling a root canal in modern times has been by the use of an endodontic obturator disclosed in U.S. Pat. Nos. 4,758,156 and 4,894,011 by Dr. William B. Johnson. These patents are incorporated herein by reference. These patents disclose endodontic obturators utilizing a carrier in the form of a shaft of solid material that is metal or plastic that has formed thereon filler material, such as gutta percha. The gutta percha is heated such as over an open Bunsen Burner or by other techniques and while in semi-liquid state, the carrier with the adhered gutta percha is inserted into the prepared root canal. This technique introduces the gutta percha into the canal and, by means of the carrier, into the full depths of the canal to the apical area. Further, the physical insertion of the carrier serves to compact and force the filler material into irregular areas of the root canal.

The technique employed in these two patents is typically in the form of an elongated tapered shaft that is inserted into and remains in the tooth root canal.

Carriers can be either metal, fiberglass or plastic and in recent years the use of plastic carriers has increased in preference by some practitioners.

The present invention is directed towards an improved system for filling an endodontically prepared root canal. Additional background material relating to the endodontic preparation of root canals and filling root canals can be obtained from the following previously issued United States and foreign patents and technical art:

| PATENT NO. | INVENTOR | TITLE |
| --- | --- | --- |
| 674,419 | Kinsman | Root Canal Filling For Teeth |
| 1,463,963 | Miller | Root Canal Point |
| 1,469,992 | Card | Dental Root Canal Point |
| 1,969,808 | Lentulo | Rotary Plugging Tool |
| 3,318,000 | Paris | Dental Root Canal Filling Point |
| 3,534,476 | Winters | Method and Apparatus for Drilling and Filling Root Canals |
| 3,813,779 | Tosti | Method and Apparatus for Sealing Root Canals and Anchoring Teeth |
| 3,861,043 | Lieb et al. | Dental Pin |
| 4,353,698 | McSpadden | Dental Tool |
| 4,397,634 | Biggs | Surgical Pins and Method |
| 4,457,710 | McSpadden | Dental Instrument |
| 4,480,996 | Crovatto | Endodontic Instrument for Dental Root Canal Filling |
| 4,758,156 | Johnson | Tool for Use in Applying Filler Material to an Endodontically Prepared Root Canal |
| 5,051,093 | Fitzmorris | Root Canal Filling Device Including Releasably Reusable Inserter Tool |
| CA 1220369 | Weisskircher | Self-Adapting Retentive Endodontic Build-Up Post |
| CH 513640 | Corneo | Instrument for Filling Dental Root Canals |
| DE 126184 | Beust | Dental Root Filling |
| FR 775073 | Garnier | Filling Paste for Sealing Obturations of the Tooth Crevice |
| FR 2,163,953 | Aubert & Gluck | Obturator Root |

Other Cited References:

| | | |
| --- | --- | --- |
| Vol. 4, No. 6 | Journal of Endodontics-June 1978 | |
| Vol. XXV, P. 185–195 | New York Odontological Society | The Dental Cosmos |
| Third Edition, P. 271–272 | Endodontics- Ingle and Taintor | Obturation of the Radicular Space |
| Jan. 1, 1980 | British Dental Journal- Negm, Grant et al. | A Newly Designed Root Canal Filling Material |
| January, 1983 | Oral Surgery- Negm | Filing Root Canals with Silver-Percha Cones: A Clinical Study |

BRIEF SUMMARY OF THE INVENTION

The invention herein is an obturator system for filling an endodontically prepared root canal in a tooth. The system uses an obturator in the form of an elongated heat conductible shaft having a proximal and a distal end. Filler material, such as gutta percha, is formed on the shaft distal end portion. The shaft distal end portion with the gutta percha material thereon is inserted into a prepared root canal, the shaft serving as a vehicle for carrying the filler material into the lowermost portion of the root canal and compacting the filler material in the canal. A heater as employed in association with the shaft to heat the shaft before or after the filler material has been inserted into a root canal plasticize the gutta percha and decrease the surface tension between the shaft and the filler material. After the shaft is heated, it can be removed leaving the filler material within the tooth root canal.

The shaft of an obturator can be heated electrically such as by resistance heating employing wires attached to the shaft. In addition, the shaft can be heated electromagnetically by employing wire coiled around the shaft proximal end portion. The coil is subjected to an AC current to create an alternating electromagnetic field to heat the shaft. Further, the shaft can be heated by subjecting it to electromagnetic waves such as from a laser or other generator.

The temperature of the shaft may be sensed and indicated or a signal generated from a temperature sensor may be employed to control the heater to terminate heating when the shaft has reached a preselected temperature.

A better understanding of the invention will be obtained from the following description and claims, taken in conjunction with the attached drawings.

DESCRIPTION OF THE DRAWINGS

FIG. 1 is an elevational view of an embodiment of the invention showing a heat conductible shaft for use as a part of an endodontic obturator system. The shaft has contact points attached at spaced apart points by which electrical energy can be supplied to the shaft to cause it to heat.

FIG. 2 is an elevational view as in FIG. 1 but showing the obturator having filler material formed thereon as it appears prior to insertion into a root canal. FIG. 2 further shows additional wires leading from a temperature sensor.

FIG. 3 is an elevational view of a shaft for use as an endodontic operator similar to FIG. 1 but showing a different way of attaching conductors to the shaft.

FIG. 4 is a cross-sectional view taken along the line 4—4 of FIG. 3 showing one electrical attachment.

FIG. 7 is an elevational view of an alternate embodiment of the system for filling a root canal in which the shaft is heated by a coil of wire surrounding it.

FIG. 8 is a cross-sectional view taken along the line 8—8 of FIG. 7 showing the shaft proximal portion with the inductance coil thereon, the shaft proximal portion and the coil being encompassed within insulative and/or protective plastic.

FIG. 9 is an elevational cross-sectional view of a tooth of the type shown in FIGS. 5 and 6 and showing an alternate embodiment of the invention wherein the shaft is heated by a removable inductance coil. That is, wherein the coil may be inserted onto the shaft proximal portion before or after the proximal portion having filler material thereon is positioned within a root canal. By the application of AC current the shaft is heated. Thereafter the coil can be removed and the shaft separately removed to leave the filler material within the root canal. FIG. 10 is an elevational cross-sectional view of a shaft having filler material thereon shown in cross-section and showing the use of a laser transmitting electromagnetic wave energy that impinges upon the shaft by which the shaft may be heated to allow the shaft to be extracted while leaving the filler material within a root canal.

FIG. 11 is a rudimentary block diagram of circuitry employed to control heating of a shaft of an endodontic obturator.

FIG. 12 is an enlarged cross-sectional view of a lower portion of a shaft for use as a part of an endodontic obturator system in which the central electrically conductive shaft has insulation thereon covering a major portion of the length of the shaft and an outer electrically conductive covering. This arrangement provides for a direct flow path of electrical current that carries the full length of the shaft to the proximal end portion.

FIG. 13 is a cross-sectional view taken along the line 13—13 of FIG. 12.

FIG. 14 is a cross-sectional view taken along the line 14—14 of FIG. 12.

DETAILED DESCRIPTION OF A PREFERRED EMBODIMENT

Figures 5, 6:
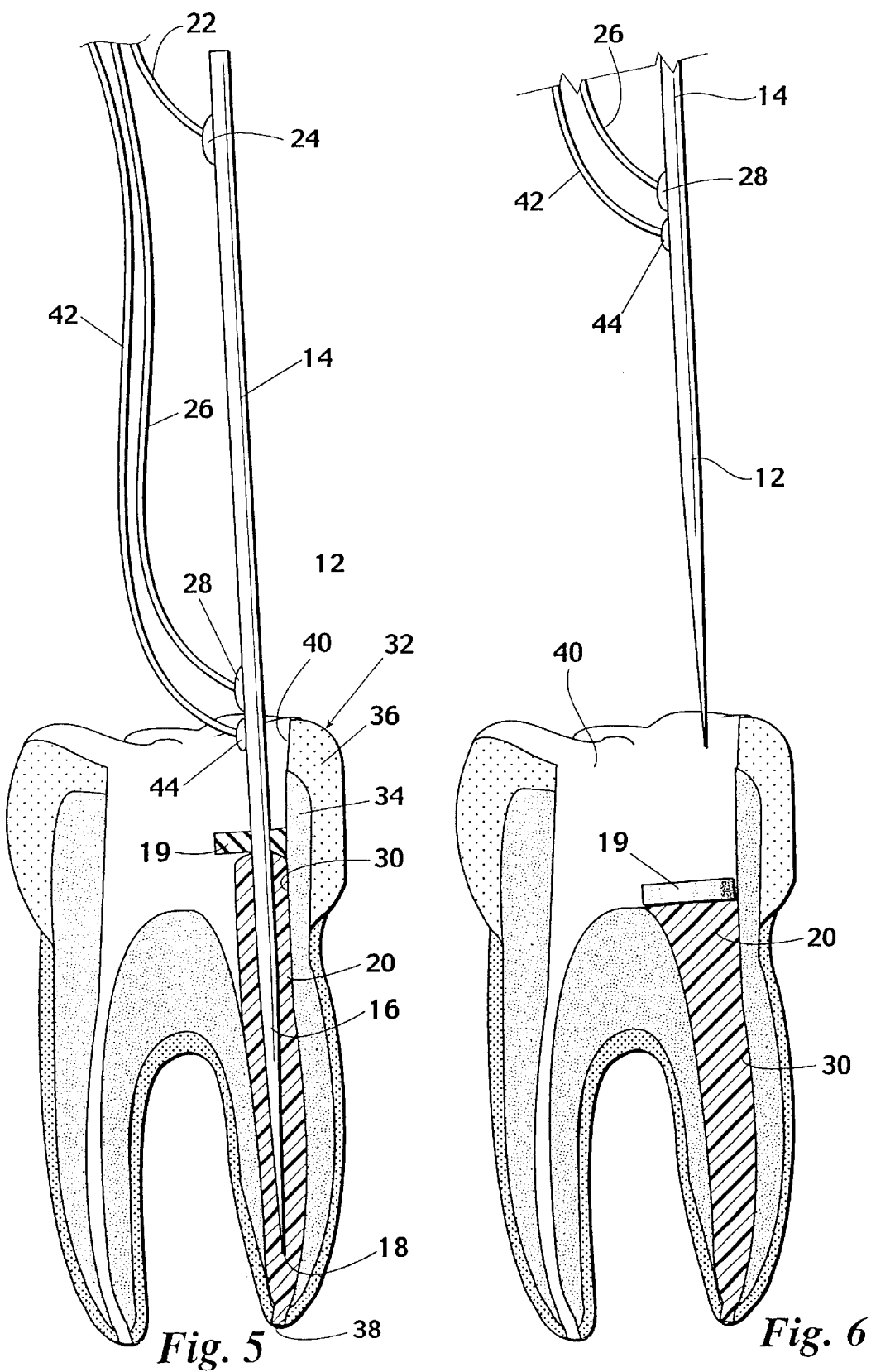
FIG. 5 shows a representative molar tooth in elevational cross-section and shows the obturator of FIG. 2 inserted into an endodontically prepared root canal in the tooth. Electrical current is applied by conductors to heat the shaft to decrease the surface tension between the exterior of the shaft and the filler material.
FIG. 6 shows the view as in FIG. 5 with the shaft removed from the tooth leaving the filler material in place to fill the root canal.

A basic concept of the invention is illustrated in FIGS. 1 and 2. The use of endodontic obdurators to fill prepared root canals in a tooth is well known and such products are commonly available on the marketplace. Endodontic obdurators are used by a high percentage of practicing endodontists and dentists that do endodontic work although other ways of filling root canals are also practiced. FIGS. 1 and 2 show an elongated shaft 12 having a proximal portion 14 and a distal portion 16, the distal portion terminating in a pointed end 18. Shaft 12 is preferably flexible so that it can bend as necessary when inserted into a root canal. Shaft 12 or at least the proximal portion 16 may have a matte finish or roughened surface to help retain filler material.

A small, elastomeric washer, commonly used on endodontic obdurators, is slidably positioned on a shaft 12. Washer 19 is used to retain filler material in a root canal when the shaft is extracted.

FIG. 2 shows shaft 12 as it is typically and commercially practiced that is, with filler material 20 preformed on the shaft distal portion 16. The shaft is, according to commonly applied current practice, typically left within the root canal. This is accomplished by cutting off the extending proximal portion 14. After completion of an endodontic procedure the opening formed in the tooth coronal area that provides access to the root canal is filled, thus encapsulating the remaining portion of shaft 12 so that no part of shaft 12 extends beyond the tooth. Shaft 12 is normally left in the root canal because the surface tension between the shaft proximal portion 16 and filler material 20 is such that if the shaft is withdrawn a substantial portion of the filler material is also withdrawn, thereby possibly leaving insufficient filler material in the root canal. Some practitioners believe there is no reason that the shaft portion of the filler apparatus should not be left within a tooth upon completion of the endodontic procedure but other practitioners dislike leaving the solid object, whether metal or plastic that functions as the shaft within the tooth. This invention provides a way the shaft can be withdrawn from a root canal without withdrawing a significant portion of the filler material. By heating shaft 12 before or after the filler material has been carried into the tooth the surface tension between the shaft and filler material can be reduced to the point that the shaft can be extracted while carrying with it only a small percent of the filler material. Thus an objective of this invention is to provide an obturator for filling an endodontically prepared tooth root canal including an elongated heat conductible shaft 12 having a proximal end 14 and a distal end 16 and having filler material 20 on the shaft distal end portion 16, the shaft with the filler material thereon being insertable into a tooth root canal and including a heater system associated with and serving to selectably heat the shaft.

In the embodiment illustrated in FIGS. 1 and 2, a first electrical conductor 22, that is a wire having insulation thereon, is attached to the shaft proximal portion 14, such as by means of welding or brazing 24. A second conductor 26 is attached to the shaft at a place that is spaced from the point of attachment of the first conductor, the second conductor being also attached by means of welding or brazing 28.

FIG. 5 shows the obturator of FIG. 2 used for insertion of filler material 20 in a root canal 30 formed in a tooth, generally indicated by the numeral 32. Tooth 32 is representative of a molar, that is a tooth that has more than one root canal as contrasted with an incisor that usually has only a single root canal. Tooth 32 is formed of dentine 34 with the upper or coronal portion covered by enamel 36. Each root of the tooth extend to an apical area 38, an opening in the bottom of the root through which nerves, blood vessels and so forth communicate with the tooth. The root canal 30 is filled with pulpal material consisting of nerves, blood vessels and so forth. As long as this material remains healthy the pulpal material can remain in the tooth indefinitely, however, if the pulpal material in the root canal 30 becomes infected, that is, abscessed, the bacterial action of the abscess builds up pressure and a toothache ensues that can be very debilitating. In the past, the only permanent remedy for a toothache caused by an abscessed tooth was to extract the tooth but now, due to the progress of modern dentistry, it is usually not necessary to extract the tooth but instead the tooth is saved by the practice of endodontics that is, by removing the abscessed pulpal material from the root canal and filling it thereby allowing the patient to maintain the tooth for all the advantages that accrue compared to a missing tooth that normally must be replaced by a false or imitation tooth. To clear out the root canal 30 an opening 40 is formed in the tooth coronal area to allow access to the root canal or canals. After the dentist or endodontist has cleaned out or reshaped the root canal 30 and it has been properly filled with filler material, the opening 40 in the tooth coronal area is effectively closed. It is important that the canal be completely, or at least substantially filled with filler material to prevent the entrance of body fluids which can become infected. The filling procedure preferably takes place all the way down the root canal to the apical area 38. Getting the filler material down to the apical area is a difficult part of filling a prepared root canal and thus the importance of an obturator or the use of a shaft 12 as illustrated in FIG. 5.

After the root canal has been cleaned and shaped and shaft 12 with filler material 20 thereon is inserted into the root canal as seen in FIG. 5, in the practice of this invention it is then required to heat the shaft 12 to raise the temperature thereof sufficient so that it can be removed from the tooth without drawing with it any substantial amount of the surrounding filler material 20. To heat the shaft, electrical energy (either AC, DC or pulsating DC) is supplied by conductors 22 and 26 to cause current to flow through the shaft between the points of attachment 24 and 28. Current flow through the shaft causes the shaft to heat. The shaft 12 is formed of heat conducted material and therefore heating the shaft proximal portion 14 will result in the heat flowing in the shaft to the distal portion 16. When the distal portion 16 has reached the desired temperature a thin film of filler material 20 contacting shaft distal portion 16 is changed to a substantially liquid state, allowing shaft 12 to be removed as indicated in FIG. 6. Thus as shown in FIG. 6, root canal 30 is filled with filler material 20 and no solid shaft remains in the tooth. Washer 19, used to retain filler material 20 in the root canal is removed before opening 40 is filled.

Returning to FIG. 2 there is shown, in addition to conductors 22 and 26, a pair of conductors 42 that connect to a temperature sensor 44 affixed to shaft 12, the temperature sensor 44 being such as a very small thermalcouple. Conductors 42 can be connected to a control device such as shown diagrammatically in FIG. 11. Control device 46 includes a temperature sensing circuit 48 and a current control circuit 50. A source of voltage is fed to current control 50 by a conductor 52 that can plug into a voltage source such as a typical house current. As seen in FIGS. 1 and 2, conductors 22 and 26 can be formed into a cable indicated by the numeral 54. In FIG. 11, cable 54 is attached to the current control circuit 50 by means of a connector 56 so that the wires extending to the obturators of FIGS. 1, 2 and 5 can be readily disconnected from control device 46. Cable 54 as shown in FIG. 11 may include only conductors 22 and 26 or may also include the temperature sensing conductor 42 of FIG. 2. The temperature as sensed by temperature probe or sensor 44 is fed by cable 42 to the temperature sensing circuit 48 which operates to turn on or off or otherwise control the voltage supplied by current control circuitry 50 to cable 54 which controls the amount of current flowing through the shaft proximal portion between welds 24 and 28. The purpose of the illustration of FIG. 11 is merely to indicate, by rudimentary diagram, that heating of the proximal portion 16 of shaft 12 can be controlled electrically either by subjecting shaft 12 to a specified current for specified length of time or by detecting the temperature of the shaft to control voltage as necessary to regulate the ultimate temperature of the shaft.

FIGS. 3 and 4 show a shaft 12 as in FIG. 1, the only difference being the means by which conductors 22 and 26 are attached to the shaft. In the embodiment of FIGS. 3 and 4 mechanical connectors 58 and 60 are employed to take the place of welding or brazing as seen in FIGS. 1 and 2. Connectors 58 and 60 may consist of any kind of mechanical device that uses threaded screws (not shown) or uses compression or any other commonly employed way of mechanically attaching a conductor to another device.

FIGS. 1, 2, 3, 4 and 5 relate to a method of practicing the invention wherein shaft 12 is heated by direct flow of electrical energy through a portion of the shaft. FIGS. 7 and 8 show an alternate means of utilizing electrical energy to heat shaft 12. As seen in FIG. 7, shaft 12 having filler material 20 on the distal portion has a coil of wire 68 on the proximal portion, the coil being fed by a two wire cable 70. A common way to heat an electrically conductive item is by inductance heating, that is in which current flow is induced by means of an alternating electric field, such as established by a coil of wire. When an AC voltage is fed by a means of cable 70 to coil 68 current flow is induced within shaft proximal portion 14 causing the shaft to heat, the heat flowing by conductance to the distal portion 16 to thereby cause the shaft to release from filler material 20. FIG. 7 shows the use of temperature sensor 44 which is optional since the heating of the shaft may be accurately predictable by supplying a prescribed level and frequency of AC voltage to coil 68 for a prescribed length of time or, when a temperature sensor 44 is used the sensor can be employed in a control circuit such as shown in FIG. 11 to automatically control the level and duration of the AC current flow through the coil to properly heat the shaft.

FIGS. 7 and 8 show a plastic portion 72 encapsulating shaft proximal portion 14 and coil 68. Plastic portion 72 can also function as a handle to aid in manipulation of the obturator to assist both in the placement of the obturator in a root canal and in removal of the shaft after it has been heated. Further, plastic portion 72 guards against possible electrical contact with a patient.

The obturator in FIG. 7 can be a device for use one time or can be reused. Since the obturator is intact when the shaft 12 is extracted from the tooth, as seen in FIG. 6, the obturator can be thoroughly sterilized and reused by applying filler material 20 to the exterior surface of shaft proximal portion 14.

FIG. 9 shows another way of practicing the embodiment of FIGS. 7 and 8 in which the coil 68 is formed on a removable bobbin 74. The bobbin has integral flange portions 74A and 74B at opposed ends. Bobbin 74 is formed of non-electrically conductive material such as plastic and has an opening 76 therethrough so that the bobbin 74 can be slid onto and off of shaft proximal portion 14. In the embodiment of FIG. 9, shaft 12 having filler material 20 thereon may be positioned in an endodontically prepared root canal. After placement in the root canal a dentist or endodontist can slip coil bobbin 74 over the shaft proximal end 14. By means of conductors 78A and 78B an AC current may be applied to coil 68 to inductively heat shaft 12 in the same manner as described with reference to FIG. 7. After the shaft has been heated bobbin 74 may be removed before the shaft itself is removed from the tooth.

Positioned on the bobbin lower flange portion 74B is a temperature sensor 80 from which extends cable 82. The temperature sensor 80 is not secured to shaft 12 but is arranged to be in very close proximity to the shaft so as to efficiently detect the temperature of the shaft. Temperature sensor 80 may completely surround the shaft and is removed from proximity to the shaft when bobbin 74 is removed. Temperature sensor 80 and conductor cable 82 can extend to a control circuit such as in FIG. 11 so that in the embodiment of FIG. 9 the shaft can be heated either by applying a preselected AC voltage for preselected time or the temperature sensor 80 may be used to control the duration of the voltage or intensity or a combination of both so as to turn off the application of current when a temperature that will allow the shaft to be easily released from the filler material has been achieved.

In the embodiment of FIG. 9 bobbin 74, coil 68, temperature sensor 80 and associated conductors 78A, 78B and cable 82 can all be encapsulated in plastic if desired so that the assembly can be easily sterilized for repeated reuse. Since there is no wear and tear on the bobbin, the coil, etc. it could be reused an unlimited number of times to heat shafts after they have been inserted into a tooth. The arrangement of FIG. 8 would have the advantage of providing reusability of the most expensive components while allowing the obturator shaft 12 to be disposed of after a one time use or it could also be sterilized and reused.

An additional embodiment of the invention is diagrammatically illustrated in FIG. 10 wherein shaft 10 with filler material 20 thereon as in the previous embodiments is shown and a laser 84 is employed, the laser providing an electromagnetic beam 86 that impinges on shaft 12. In the illustrated arrangement the laser is shown impinging on the shaft proximal portion 14 that would extend exteriorly of the coronal area of the tooth being treated after the shaft has been inserted into a root canal so that the proximal portion 14 of the shaft is heated to in turn heat the shaft distal portion 16. In the embodiment of FIG. 10, laser 84 is directed so that the energy beam 86 travels uninterruptably to the shaft proximal portion to heat the shaft. An alternate embodiment of the invention utilizes a laser that directs an energy beam to the shaft distal portion 16 after the shaft has been inserted into a root canal. This requires the laser beam 86 to pass through the gum, jaw bone and tooth dentine structure before intersecting the metal shaft distal portion. By proper selection of the frequency of the signal generated by the laser 84, the shaft proximal portion may be heated directly by electromagnetic energy to the level necessary to release the filler material and permit removal of the shaft. The expression "laser" as indicated by element 84 of FIG. 10 is by example only and is inclusive of any electromagnetic radiation generator that produces electromagnetic energy impactable upon either the proximal or distal portion of a thermally conductive shaft after the distal portion has been positioned in a root canal so as to raise the temperature of the distal portion to permit removal of the shaft while leaving the filler material within the root canal. As an alternative method, element 84 may be a sonic generator to impart high frequency sound energy to shaft 12 or element 84 may be a piezoelectric device that physically vibrates shaft 12. Either system of vibration is preferably at a frequency to cause the shaft to heat.

FIGS. 12–14 show an additional alternate embodiment of the invention. FIG. 12 is a cross-sectional view that shows a shaft 12 lower portion with a pointed end 18. A substantial portion of shaft 12 except for a portion 88 extending to end 18 is covered with a layer of insulation 90 which preferably is a form of plastic. Surrounding insulation 90 and including the portion 88 of shaft 12 that is without insulation, is an outer electrically conductive sheath 92. Sheath 92 may extend beyond shaft end 18 as illustrated although it may terminate short of end 18. Electrically conductive sheath 92 can be premanufactured to fit onto shaft 12 having the insulation 90 thereon or conductive sheath 92 may be sprayed onto the shaft or otherwise applied as a coating of electrically conductive material.

In the arrangement of FIGS. 12–14 the shaft is heated by providing electrical energy between the central metal shaft portion 12 and the conductive sheath 92 as indicated diagrammatically by a voltage source 94.

The embodiment of FIGS. 12–14 is employed in the same way as has been previous described. FIGS. 12–14 do not show filler material but it is understood that filler material would be employed for insertion into a root canal of a tooth as illustrated in FIGS. 2, 5, 7, 9 and 10. After the shaft of FIGS. 12–14, having filler material thereon, is inserted into a tooth, the shaft can be heated by providing a source of electrical energy 94 that can be AC or DC or pulsed DC as previously described. Electrical energy flows in shaft 12 down to the portion 88 and then flows through conductive sheath 92. In this way, the total length of the shaft is heated by current flow through the electrical resistance imposed by the shaft and/or conductive coating 92.

In the embodiment of FIGS. 12–14 the insulation sheath 90 and conductive sheath 92 to are not required to extend the full length of shaft 12, that is the upper end portion that can receive a handle, like the handle 72 of FIG. 7, does not need to be covered with insulation sheath 90 and conductive sheath 92, since only the portion of shaft 12 that has filler material needs to be heated to enable the shaft to be withdrawn from the filler material after a root canal has been filled.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed:

1. An obturator system for filling an endodontically prepared tooth root canal comprising:

an elongated heat conductible shaft having a proximal portion and a smooth distal portion;

filler material applied onto said shaft distal portion, said shaft having sufficient rigidity to serve as a vehicle for carrying said filler material thereon and compact the filler material into the lowermost portions of a tooth root canal; and a coil of electrically conductive wire positioned around said shaft proximal portion and adjacent said distal portion having said filler material thereon, said coil having conductors extending therefrom connectable to a source of AC voltage whereby said shaft may be inductively heated to reduce surface tension of said filler material permitting said shaft to be removed to leave said filler material compacted in said root canal.

2. An obturator system according to claim 1 including:

a signal generating temperature sensor affixed to said shaft.

3. An obturator system according to claim 2 including:

circuitry attached to said temperature sensor employed to control electrical energy to said coil.

4. An obturator system according to claim 1 wherein said shaft is of metal.

5. An obturator system according to claim 1 wherein said shaft is of plastic having electrically conducive material admixed therein.

6. An obturator system according to claim 1 wherein said coil is encompassed within a non-electrically conductive body portion.

7. An obturator system according to claim 6 wherein said non-electrically conductive body portion is formed of plastic.

8. An obturator system according to claim 6 wherein said body portion forms a handle for manually manipulating said shaft.

9. An obturator system according to claim 1 wherein said coil is telescopically removable from said shaft.

10. An method of filling an endodontically prepared root canal of a tooth comprising:

applying filler material to the external surface of a distal portion of an elongated structural shaft formed of heat conducting material, the shaft having an integral generally uniform diameter proximal portion, the shaft having sufficiently rigidity to serve as a vehicle for carrying and compacting said filler material into a lowermost portion of a root canal, and having a coil of electrically conductive wire positioned around said shaft proximal portion and adjacent said distal portion, the coil having conductors extending therefrom connectable to a source of AC voltage;

inserting said proximal portion of said shaft having said filler material thereon into the root canal;

applying said AC voltage to said coil to inductively heat said shaft to decrease the surface tension of said filler material; and removing said shaft leaving said filler material in the root canal.

11. A method according to claim 10 wherein said shaft has a signal generating temperature sensor affixed thereto.

12. A method according to claim 11 including the step of controlling said AC voltage applied to said coil in response to a signal generated by said temperature sensor.

13. A method according to claim 10 wherein said coil is encompassed within a plastic body portion.

14. A method according to claim 13 in which said plastic body portion forms a handle portion and wherein said step of inserting said proximal portion of said shaft having filler material thereon into the root canal is accomplished using said handle portion.

* * * * *